(12) United States Patent
Holmquist

(10) Patent No.: US 6,730,070 B2
(45) Date of Patent: May 4, 2004

(54) ABSORBENT PRODUCT HAVING A FASTENING ARRANGEMENT

(75) Inventor: Christian Holmquist, Göteborg (SE)

(73) Assignee: SCA Hygiene Products AB, Gothenburg (SE)

(*) Notice: Subject to any disclaimer, the term of this patent is extended or adjusted under 35 U.S.C. 154(b) by 60 days.

(21) Appl. No.: 09/964,568

(22) Filed: Sep. 28, 2001

(65) Prior Publication Data

US 2002/0040214 A1 Apr. 4, 2002

Related U.S. Application Data

(60) Provisional application No. 60/236,169, filed on Sep. 29, 2000.

(51) Int. Cl.[7] .............................. A61F 13/15; A61F 13/20
(52) U.S. Cl. .................... 604/392; 604/385.3; 604/390; 604/391
(58) Field of Search ................... 604/385.01–385.06, 604/385.13–385.14, 385.201, 388.22, 385.23–387, 389–396, FOR 103, FOR 104

(56) References Cited

U.S. PATENT DOCUMENTS

| | | | | | |
|---|---|---|---|---|---|
| 3,646,937 A | * | 3/1972 | Gellert | | 604/390 |
| 3,731,689 A | * | 5/1973 | Schaar | | 604/385.13 |
| 3,800,796 A | * | 4/1974 | Jacob | | 604/390 |
| 3,989,048 A | * | 11/1976 | Cepuritis et al. | | 604/390 |
| 4,211,226 A | * | 7/1980 | Schaar | | 607/390 |
| 4,500,316 A | * | 2/1985 | Damico | | 604/389 |
| 5,797,896 A | * | 8/1998 | Schmitz | | 604/391 |
| 5,830,206 A | * | 11/1998 | Larrson | | 604/390 |
| 5,968,030 A | * | 10/1999 | Shimizu et al. | | 604/390 |
| 6,027,484 A | * | 2/2000 | Romare | | 604/386 |
| 6,036,805 A | * | 3/2000 | McNichols | | 156/227 |
| 6,110,157 A | | 8/2000 | Schmidt | | |
| 6,322,552 B1 | * | 11/2001 | Blenke et al. | | 604/540 |
| 6,454,888 B1 | * | 9/2002 | Murie et al. | | 156/64 |
| 6,508,797 B1 | * | 1/2003 | Pozniak et al. | | 604/385.11 |
| 2002/0040214 A1 | * | 4/2002 | Holmquist | | 604/385.01 |
| 2002/0138063 A1 | * | 9/2002 | Kuen et al. | | 604/391 |
| 2002/0148557 A1 | * | 10/2002 | Heller et al. | | 156/252 |
| 2002/0173768 A1 | * | 11/2002 | Elsberg et al. | | 604/391 |

FOREIGN PATENT DOCUMENTS

| | | | | |
|---|---|---|---|---|
| DE | 19732499 A1 | * | 2/1999 | |
| EP | 0 795 307 | | 9/1997 | |
| FR | 2566 631 | | 1/1986 | |
| JP | 43-49542 | * | 7/1973 | 604/389 |
| JP | 2000-14702 | | 1/2000 | |
| WO | WO 01/13844 A1 | * | 3/2001 | |
| WO | WO 01/43683 A1 | * | 6/2001 | |

* cited by examiner

*Primary Examiner*—Karin Reichle
(74) *Attorney, Agent, or Firm*—Young & Thompson

(57) ABSTRACT

The absorbent product has longitudinal side edges, transverse end edges, first and second end sections and a crotch section between the end sections. A fastening tab is arranged at a side edge, on the first end section, and includes a first fastening member. A second fastening member is arranged on the second end section and arranged to interact with the first fastening member to bind the product into a briefs shape. A material strip extends in the transverse direction of the product and is fixed permanently to the product, at least at its ends. The fastening tab constitutes part of the material strip and is demarcated from the rest of the material strip by a tear line extending substantially transversely to the direction of extent of the material strip.

9 Claims, 5 Drawing Sheets

ABSORBENT PRODUCT HAVING A FASTENING ARRANGEMENT

This application claims the benefit at U.S. Provisional Application No. 60/236,169, filed Sep. 29, 2000.

TECHNICAL FIELD

The invention relates to an absorbent product such as a nappy, an incontinence pad, or the like, having a substantially elongated shape and comprising a liquid-permeable surface layer, a liquid-tight surface layer, and an absorption body arranged between the surface layers, in addition to which the product has longitudinal side edges, transverse end edges, a first end section and a second end section and a crotch section lying between the end sections, and at least one fastening tab arranged at a side edge of the product, on the first end section, and comprising a first fastening member. A second fastening member is arranged on the second end section of the product and arranged so as to interact with the first fastening member in order to bind together the product into a briefs-like shape.

BACKGROUND

The fastening members of an absorbent product of the type stated in the introduction usually comprise a first fastening member in the form of a fastening tab arranged on each side edge adjacent to the one end edge of the product. Advantageously, the fastening tabs are folded in against the one surface layer of the product prior to use and, when the product is used, are folded out and fixed to a second fastening member arranged on the second end section. In the production of the product, the fastening tabs are often fixed close to the longitudinal side edges and are folded in around the respective side edge so as to lie against the second surface layer. A drawback with such fastening members is that at high production speeds a complicated process solution is required in order for the fastening members to end up in the correct position on the product when folded. If the fastening member comprises adhesive, moreover, erroneous foldings and misplacements can result in adhesive bits of the fastening tabs becoming jammed in the equipment.

OBJECTS AND MOST IMPORTANT CHARACTERISTICS OF THE INVENTION

One object of the present invention is to achieve a fastening member which, in the production thereof or in the application thereof to an absorbent product, does not require complicated folding operations. A second object of the invention is to offer a fastening system which does not require a folding operation in the application of the fastening system to an absorbent product or in the production of the fastening system. A further object is to make it easier to fix a fastening member to an absorbent product and hence lower the risk of misplacements of the fastening member, so that fewer defective products need to be discarded in the course of production and material wastage can thereby be reduced.

According to the invention, a product of the type discussed in the introduction has been achieved, which product is primarily characterized in that the fastening tab constitutes a part of a material strip which extends in the transverse direction of the product and the material strip is fixed permanently to the product, at least at its ends, and in that the fastening tab is demarcated from the rest of the material strip by means of a tear line extending substantially transversely to the direction of extent of the material strip.

In particular, the invention is directed to an absorbent product having a substantially elongated shape and further comprising a liquid-permeable surface layer, a liquid-tight surface layer, and an absorption body arranged between the surface layers, in addition to which the product has longitudinal side edges, transverse end edges, a first end section, a second end section, a crotch section lying between the end sections, a material strip which extends in the transverse direction of the product and which material strip is fixed permanently to the first end section, at least at its ends, a fastening tab constituting a part of the material strip and demarcated from the rest of the material strip by means of a tear line extending substantially transversely to the transverse direction of extent of the material strip, the fastening tab including a first fastening member and the product further comprising a second fastening member arranged on the second end section of the product and arranged so as to interact with the first fastening member in order to bind together the product into a briefs shape.

Suitable tear lines are perforations, notches or cuts through the whole or part of the thickness of the material strip, compressions, chemically or physically produced material weakenings, tear bands, etc. According to a preferred embodiment of the invention, the tear line comprises a perforation or other material weakening.

The material strip which forms the fastening tab can be fixed to the liquid-tight surface layer, i.e. to the surface of the product which is intended to be facing away from the user during use. Alternatively, the material strip can be fixed to the liquid-permeable surface layer, i.e. to the surface of the product which is intended to be facing the user during use. Especially in the latter case, the parts of the material strip which are expected to be in direct contact with the skin of the user during use of the product, should be formed by a material which does not chafe or otherwise irritate the skin. Suitable such materials are, for example, non-woven strips, or other textile or textile-like materials.

The material strip can comprise elastic material and can in this case form part of the waist elastics of the product, i.e. elastic members arranged around the transverse edges of the product which, during use, form the waist opening of the product. The waist elastics gives the product an elastic, stretchable waist edge and is intended to achieve improved fit and tightness of the product around the waist of a user. Alternatively, a wholly or partially elastic material strip can, of course, simply constitute the waist elastics of the product.

The fastening member of the product can comprise a mechanical fixing member. Usable mechanical fixing members are, for example, VELCRO surfaces (hook members/loop members), snap fasteners, clasp/eye, button/buttonhole, or the like. Adhesive fixing members can, however, be used, in which case the first fastening member expediently comprises adhesive fixing tabs arranged on the first end section of the product and the second fastening member comprises at least one receiving surface for the fixing tabs, arranged on the second, opposite end section of the product. Combinations of mechanical and adhesive fastening systems are also conceivable within the scope of the invention.

To prevent the fastening members from attaching to an unwanted part of the product in the course of production or prior to use, it is expedient for adhesive parts of the fastening members to be protected, prior to use, by a detachable protective layer, which is removed before the product is bound together around the body of a user. It can also be expedient to cover clasp-type, mechanical fastening members with a protective layer to prevent erroneous fastening and protect the fastening members from dirt.

It is generally expedient for the absorbent product to have a symmetrical design, with at least a first fastening member arranged on each side edge of the product.

The fastening tab, or at least one of the fastening tabs arranged on each side edge, can constitute a part of the same material strip, which thus extends transversely across the product, or can constitute a part of a first material strip arranged on one of the side edges and a second material strip arranged on the other side edge.

The fastening system thus expediently comprises a first part having a first fixing member, which preferably is mechanical or adhesive, and a second part having a second fixing member, which comprises at least one receiving surface for the first fixing member. Such a receiving surface can be a part of a surface layer belonging to the product or can be constituted by a separate material fixed to a surface layer belonging to the product. As the receiving surface for mechanical fixing members (hook members or loop members), a corresponding, complementary hook or loop type fixing member is preferably used. As the hook members, surfaces having hook-like or clasp-like projections are preferably used and, as the loop members woven, braided, crocheted or knitted textile materials, having projecting material loops in which the clasp members can attach, are used. Unwoven fibre fabrics, so-called non-woven materials, may also be used as loop members. Suitable fibre fabrics are in this context relatively loose materials having a multiplicity of fibre elements which can serve as fixing means for hook members.

The fastening system according to the invention can comprise both adhesive and VELCRO fixing members, as well as fixing members having fixing surfaces which exhibit both adhesiveness and friction, or engagement capacity. Examples of the latter type of fastening member are adhesive surfaces having spike-like fixing elements which project through the adhesive. Such a fastening member attaches well to a textile or other porous receiving surface and combines adhesion with mechanical locking as a result of the partial penetration of the spike-like fixing elements into the receiving surface, whereupon the adhesive is brought into fixing contact with the receiving surface.

As a result of the fastening tabs according to the invention being formed by tearing open along a preformed tear line in a surface material, the tabs can be easily handled and continually applied in a production process. No loose protruding tabs are at risk of becoming jammed in the production equipment. Moreover, complicated fold stages during the production are avoided. By choosing the shape of the tear line, the tab can be given any desired shape. A curved tear line can in this case be preferable, since the fastening tab thereby acquires a rounded demarcation edge which makes the tab easier to grip and reduces the risk of sharp or abrasive corners being formed.

BRIEF DESCRIPTION OF THE FIGURES

The invention will be described in greater detail below with reference to the embodiments shown in the appended drawings, in which.

DESCRIPTION OF ILLUSTRATIVE EMBODIMENTS

Figure 1:
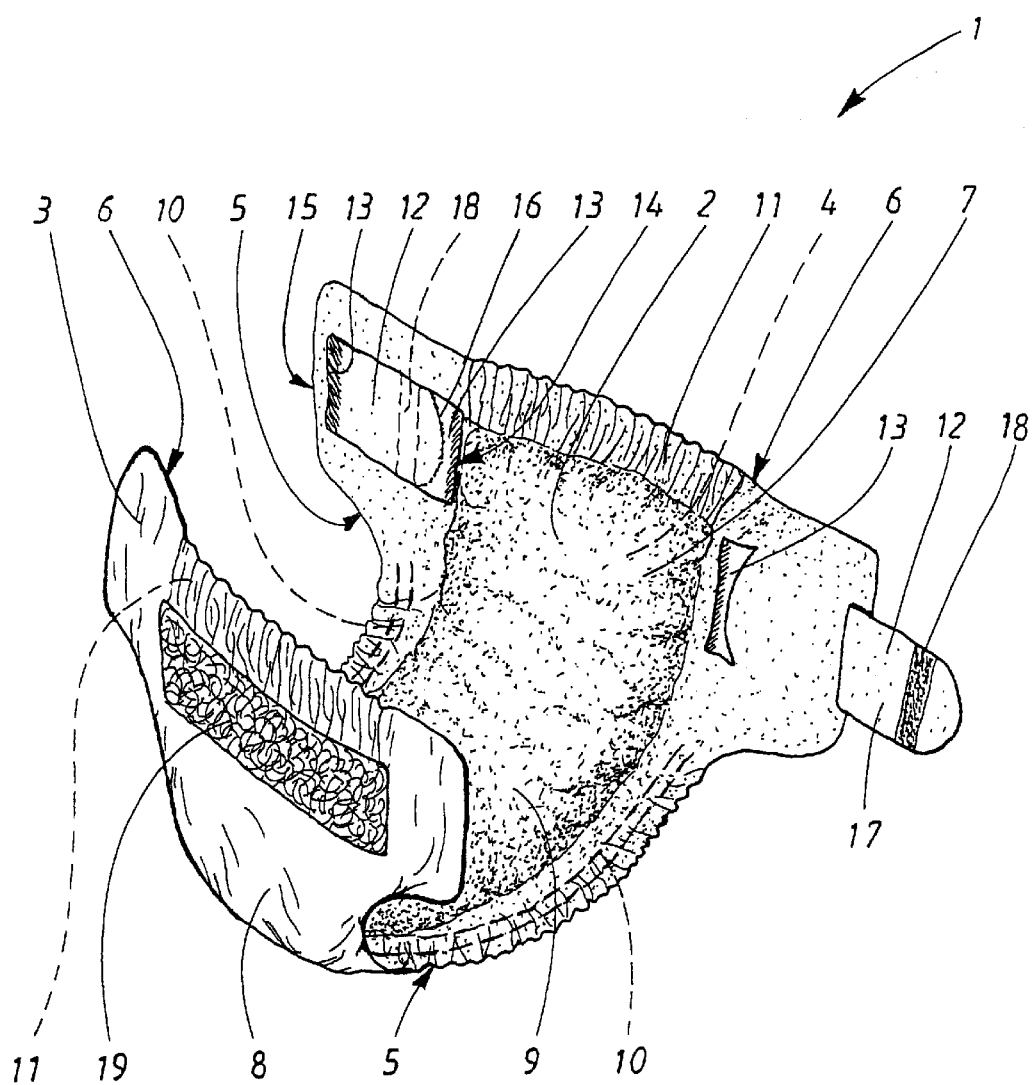
FIG. 1 shows a nappy according to one embodiment of the invention.
Figure 2:
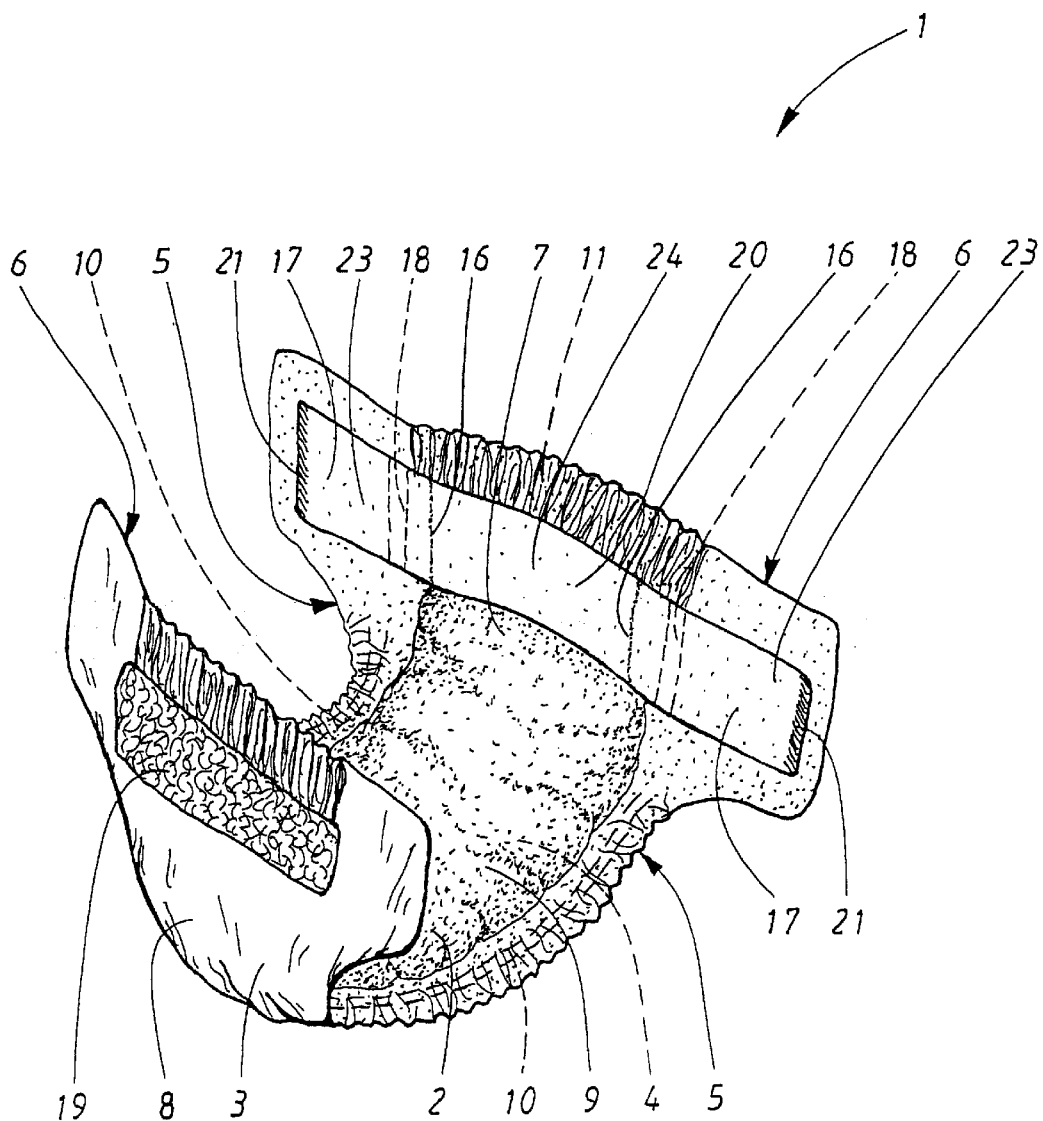
FIG. 2 shows a nappy according to a second embodiment of the invention.

The nappies 1 shown in FIGS. 1 and 2 have a substantially elongated shape and comprise a liquid-permeable surface layer 2 which is facing the user during use, a liquid-tight surface layer 3 which is facing away from the user during use and an absorption body 4 arranged between the layers. The nappies further have longitudinal side edges 5, transverse end edges 6, a first end section 7, a second end section 8 and a crotch section 9 situated between the end sections 7, 8. Elastic members 10 are placed along each side edge 5 in the crotch section 9 and form leg elastics. In addition, elastic members 11 are arranged along a part of each end edge 6 and form waist elastics.

The materials used for the various components included in the nappies are conventional in type. The liquid-permeable surface layer 2 is thus expediently constituted by a liquid-permeable non-woven material, a perforated plastics film, a gauze, or the like. The liquid-tight surface layer 3 is expediently a thin plastics film, a liquid-tight non-woven material or the like. It is also customary to use a laminate of a plastics film and a non-woven material. The non-woven material is arranged on the side of the liquid-tight surface layer 3 which is facing away from the absorption body 4, whereby a textile surface is obtained on the outside of the nappy. Such a textile surface is advantageous for a number of reasons. For instance, it is nicer to wear in contact with skin, reduces the risk of undesirable rustling noise and increases the surface friction of the layer, which means that underwear or other clothes stay more securely in place over the nappy. Moreover, a textile surface layer can be used as the fixing surface for a hook or loop type fixing member. The absorption body 4 can be made up of one or more layers of absorbent material, such as cellulose fluff material, tissue, absorbent foam, etc. It is also usual for the absorption body to contain super-absorbents, i.e. polymer materials which can absorb body liquid equivalent to many times their own weight with the formation of a hydrogel. While such super-absorbents are usually present in the form of particles, fibres, flakes, granulates and film can also used. In addition, the absorption body 4 can comprise non-absorbent components such as stiffening elements, shaping elements, binding fibres, binding agents, etc. Different types of liquid-receiving porous structures, such as fibre wads or the like, can be included in the nappy 1. The elastic members 10, 11 can be one or more elastic ribbons or threads, elastic non-woven materials, etc.

FIG. 1 shows an embodiment according to the invention having two separate material strips 12, which extend in the transverse direction of the nappy 1 and are placed parallel with the end edge 6 close to each longitudinal side edge 5 of the first end section 7 on the side of the nappy 1 which is facing the body of the user during use. Each material strip 12 is fixed permanently to the nappy by its ends, with glued sections 13 along an inner edge 14 and an outer edge 15 of the strip 12, the edges 14, 15 extending substantially in the same direction as the longitudinal side edges 5 of the nappy. The material strips can, of course, be fixed to the nappy in other known ways, for example by welding. Close to the inner longitudinal edge 14 of each material strip, the strip is provided with a perforation 16 enabling detachment of a fold-out tab 17 which is demarcated from the rest of the strip 12 by means of the perforation 16. After the respective tab 17 has been detached from the respective strip 12 by tearing along the perforation 16, the tab can be folded out once the strip has been fastened along its outer edge 15, as is shown on the one side of the nappy in FIG. 1.

Each tab 17 comprises a first fastening member 18 in the form of a VELCRO tape on one side of the tab 17, which, prior to being folded out, is facing the nappy. After the nappy has been put on and the tabs 17 have been folded out, the first fastening members 18 are fixed to a second fastening member 19, which in FIG. 1 is in the form of a loop material having thread-like fibres in which the hook members of the VELCRO tape 18 can hook. Suitable looped materials are in this case woven, knitted, crocheted textile materials having looped elements, or non-woven materials having fibre elements in which the hook members of the first fastening members 18 can hook. The second fastening member 19 in this case constitutes a receiving surface for the VELCRO tape 18 and is placed on the second end section 8 on the side of the nappy 1 which is facing away from the body of the user during use. In the example shown, the receiving surface is a separate material piece which is fixed to the outside of the liquid-tight surface layer 3. It is alternatively possible, however, to use the liquid-tight surface layer 3 as the receiving surface, for example when the liquid-tight surface layer 3 has a textile or textile-like outer surface of fibres or threads in which the hook members of the first fastening member 18 can attach. In addition, the receiving surface can be a plurality of smaller, separate material surfaces, which together form a receiving surface for the first fastening members 18.

FIG. 2 shows a second embodiment of a nappy according to the invention. In FIG. 2, a continuous material strip 20, which extends in the transverse direction of the nappy, is fixed by its ends 21 to the first end section 7 close to each side edge 5 of the nappy, the strip extending over the liquid-permeable surface layer 2 along the main part of one of the end edges 6. The strip 20 is provided with two perforation lines 16, symmetrically arranged with one perforation line 16 on each side of a longitudinal line extending centrally through the nappy, the strip 20 being divided by the perforations 16 into two outer sections 23 and a central section 24.

Following tearing along the pertorations 16, the central section, which is not fixed to the nappy 1, is removed, whereas the two outer sections form fold-out tabs 17, each tab 17 being demarcated from the rest of the strip 20 by means of the perforations 16. Each tab 17 is provided with a first fastening member 18 in the form of a VELCRO tape on one side of the tab 17 which is facing the nappy before the tab 17 is folded out. The second end section 8 comprises a second fastening member 19 in the form of a VELCRO tape on the side of the nappy 1 which is facing away from the user during use. When the nappy is fastened on a user, the first fastening members 18 are fixed to the second fastening member 19.

The strip 20 can alternatively be provided with a centrally arranged perforation, whereby the strip is divided into two outer sections, each section forming a fold-out tab after the perforation has been torn along. Each tab is demarcated from the rest of the strip by means of the perforation. Such an embodiment makes it possible to obtain relatively long fastening tabs 17, which can be an advantage, since the nappy 1 can consequently be used by users of different body size. In order further to increase the adjustability of the nappy in respect of size, a plurality of fastening members 18 can be arranged along the fastening tabs 17.

Figure 3:
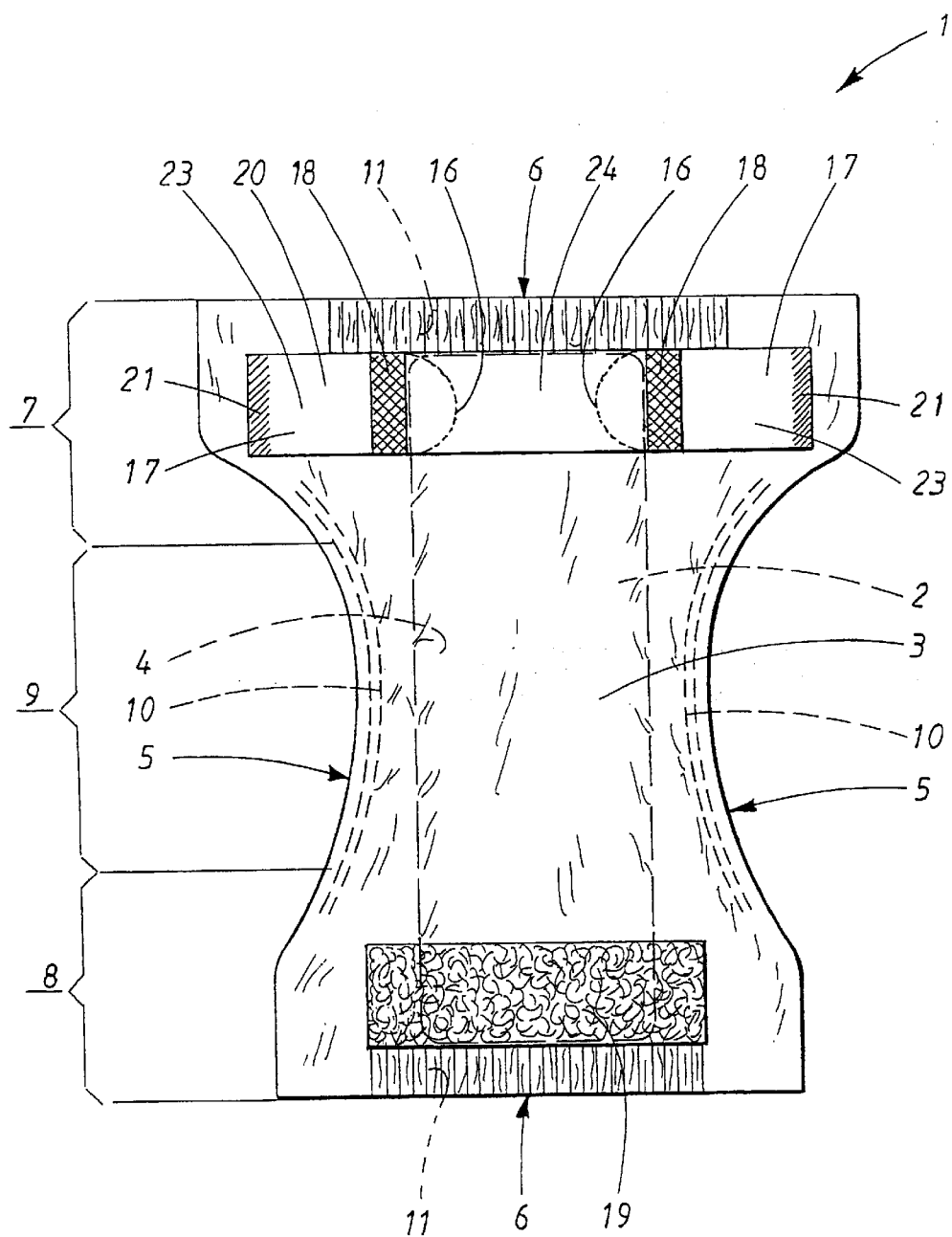
FIG. 3 shows a nappy according to a third embodiment of the invention.
Figure 4:
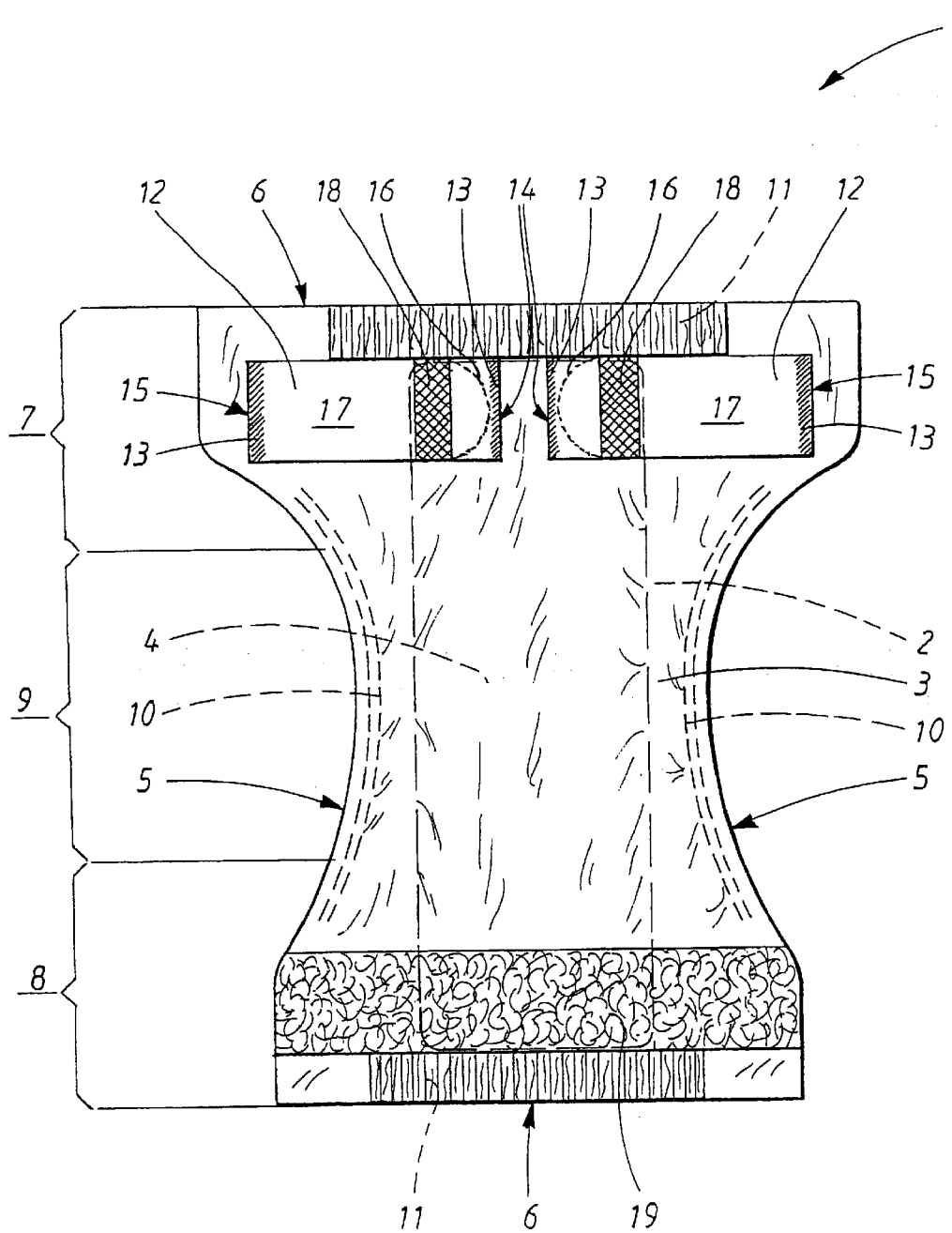
FIG. 4 shows a nappy according to a fourth embodiment of the invention.

FIGS. 3 and 4 each show a nappy 1 having substantially the same structure as the nappies in FIGS. 1 and 2 and having the liquid-tight layer 3 facing outwards. Each nappy has longitudinal side edges 5, transverse end edges 6, a first end section 7, a second end section 8 and a crotch section 9 lying between the end sections 7, 8. Each nappy comprises elastic members 10, which form leg elastics along the longitudinal side edges 5, and elastic members 11, arranged along the transverse end edges and forming waist elastics.

In FIG. 3, a material strip 20, which extends in the transverse direction of the nappy 1, has been fixed permanently, for example by gluing or welding, by its ends 21 to the first end section 7 close to each side edge 5 of the nappy, the strip extending centrally along the greater part of the one end edge 6. The strip 20 has been fixed to the nappy on the liquid-tight surface layer 3, i.e. on the side of the nappy which is facing away from the user during use. The strip 20 has two perforations 16, whereby the material strip 20 is divided into two outer sections 23 and an intermediate central section 24. The two outer sections 23 each comprise a fastening member 18 in the form of a VELCRO tape having a fixing surface facing outwards from the nappy. After the perforations have been torn along, the central section 24 is able to be removed, whereupon two fold-out tabs 17 are formed. Alternatively, the central section 24 can be fixed to the liquid-tight surface layer 3 by gluing, or welding.

Such a securement does not need to be as strong as the securements at the ends 21 of the material strip, since it plays no part in the fastening of the nappy on a user. A fastening in the form of a pattern of fastening regions, for example dots or lines, is therefore generally adequate. The fold-out tabs 17 are intended to be fastened to a second fastening member 19, which is arranged on the second end section 8 on the side of the nappy which is facing away from the user during use. Alternatively, the material strip 20, as described in connection with the nappy shown in FIG. 2, can be provided with only one centrally arranged perforation, enabling the detachment of two fold-out tabs comprising fastening members.

FIG. 4 shows a fourth embodiment according to the invention, having a material strip 12 which extends in the transverse direction of the product close to each longitudinal side edge 5 on the first end section 7 of the liquid-tight surface layer 3, i.e. on the side of the nappy which is intended to be facing away from the body of the user during use. Each material strip 12 has been fixed at its ends to the nappy with glued sections 13 along an inner edge 14 and an outer edge 15 of the strip 12, which edges 14, 15 extend in the same direction as the longitudinal edges 5 of the nappy.

Each strip 12 has a perforation 16 close to the inner edge 14, which perforation 16 enables the detachment of a fold-out tab 17 from the nappy. Each tab 17 comprises a first fastening member 18 in the form of a VELCRO tape on the side of the tab 17 which is facing away from the nappy 1 before the tab 17 is folded out. On the second end section 8, a second fastening member 19 is arranged, on the side of the nappy 1 which is intended to be facing away from the user during use. The second fastening member 19 is a receiving surface for the fastening members 18 arranged on the tabs 17 and is therefore intended to interact with the first fastening members 18 in order to bind together the product into a briefs-like shape.

The second fastening member 19, instead of being formed by a separate material piece as in the illustrative embodiment shown, can also, of course, be constituted by the outer liquid-tight surface layer. The liquid-tight surface layer shall in this case have a fibrous, textile, or textile-like surface on the surface facing away from the user. Such a surface means that fastening members in a VELCRO tape or a hook or loop type material comprising the first fastening member can hook onto threads or fibres in the surface layer. Alternatively, each fold-out tab can have a fibrous textile-like surface, intended to cling to the second fastening member, which is here constituted by a VELCRO tape provided with hook members. As previously discussed, types of mechanical fastening other than VELCRO tape, such as snap fasteners or the like, can also, of course, be used within the scope of the invention.

Instead of VELCRO tape or hook or loop type fixing members, the first fastening member can be constituted by an adhesive intended to stick to the second fastening member, which in this case constitutes a receiving surface. Such a receiving surface can either be a part of the liquid-tight surface layer or can be configured as a reinforced region on the liquid-tight surface layer. Alternatively, the fold-out tab can comprise a fixing surface, intended to constitute a support to which an adhesive layer of the second fastening member shall stick.

In order to prevent inadvertent and erroneous attachment to the nappy before the tab is to be used, adhesive and/or hook-shaped fixing members are expediently provided, prior to use, with a protective material arranged over the fixing surface. Such a protective layer also prevents the fixing member from becoming dirty and losing its fixing capacity. The protective material is removed before the fixing member is to be used to bind together the nappy.

Figure 5:
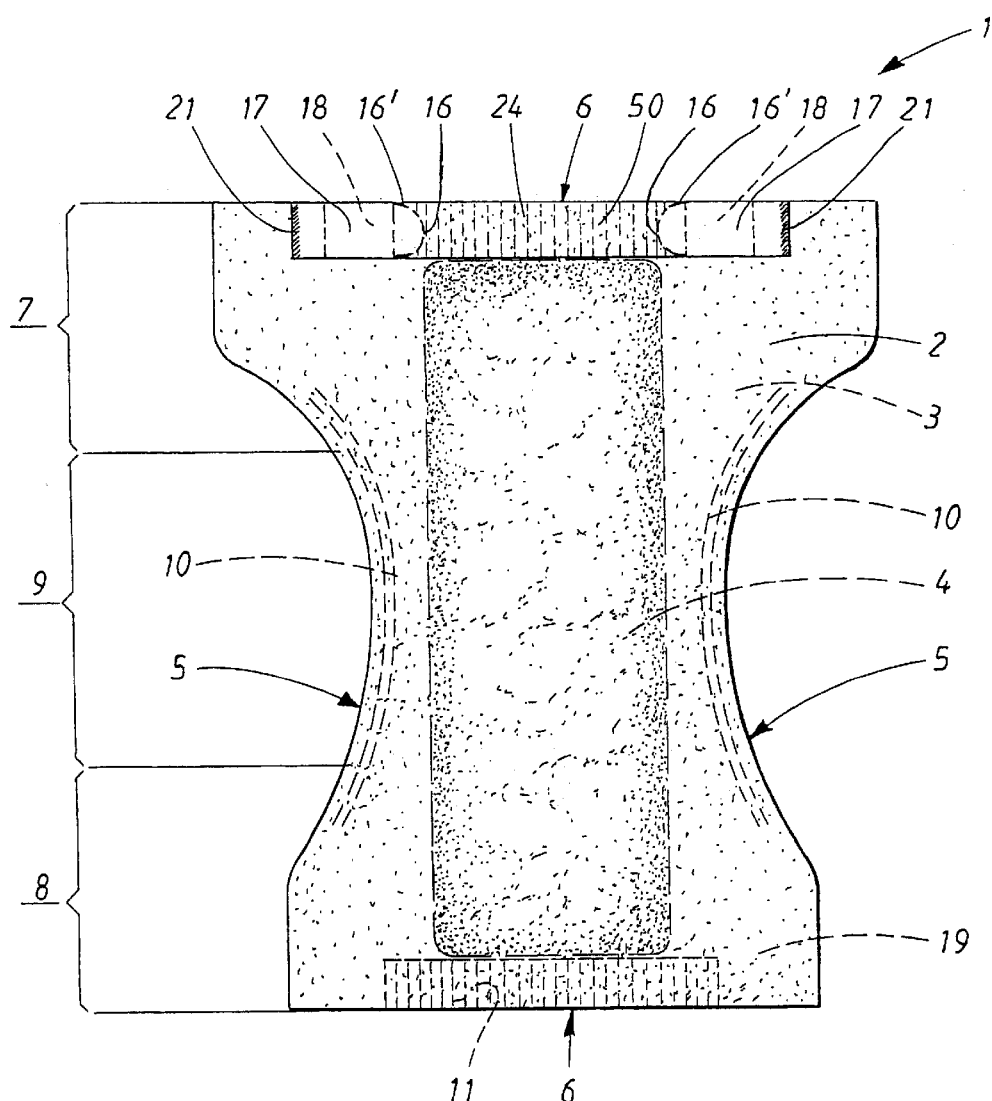
FIG. 5 shows a nappy according to a fifth embodiment of the invention.

The nappy shown in FIG. 5 also has a substantially elongated shape and comprises a liquid-permeable surface layer 2, which is facing the user during use, a liquid-tight surface layer 3, which is facing away from the user during use, and an absorption body 4, which is arranged between the surface layers 2, 3. The nappy further has longitudinal side edges 5, transverse end edges 6, a first end section 7, a second end section 8 and a crotch section 9 situated between the end sections.

Viewed from the side which is intended to be facing the user during use, FIG. 5 shows a fifth embodiment according to the invention, having an elastic material strip 50 which extends in the transverse direction of the nappy and is placed adjacent to one of the transverse end edges 6 on the side of the nappy which is facing the body of the user during use. The elastic material strip 50 is provided with perforations 16 for the detachment of two fold-out tabs 17 from the strip 50, each tab 17 being demarcated from the rest of the strip 50 by means of a perforation 16. The material strip 50 is fixed permanently to the nappy 1, for example by glue or welding, at the ends 21 of the strip 50 and within a central section 24 between the perforations 16, which section does not constitute part of the fold-out tabs 17. Other fixing methods which are known within the technical field can be used to fix the material strip 50 to the nappy. A section 16' of the perforation 16 can be cut to make it easier to grip the tab which is to be folded out. Each tab 17 comprises fastening members 18 in the form of a VELCRO tape, which, prior to the folding-out, is placed on the side of the tab 17 which is facing in towards the nappy.

A second fastening member 19 is provided in the form of an outer layer of non-woven material, which acts as a receiving surface for the first fastening members 18. The non-woven material can advantageously be arranged over the whole of the outer surface of the nappy 1, whereby the nappy 1 has an attractive textile outer surface. In such an embodiment, the non-woven material can also serve as a receiving member for the fastening members 18 of the tabs 17 when these are used to bind together a folded-up or rolled-up nappy after use. Alternatively, the non-woven material, or another looped material, can be arranged over just a part of the outer surface of the nappy, for example as a band-shaped region, in a manner similar to that depicted in the previously described embodiments. In FIG. 5, the nappy 1 is provided with a separate elastic member 11, which forms waist elastics on the first end section 7 of the nappy. Obviously, however, it is possible instead, or as a complement, to use an elastic material for the receiving region 19, so that this material can also serve as waist elastics. On the opposite end edge, it is obviously also possible to arrange separate elastic which is not a part of the fastening system.

Figure 6:
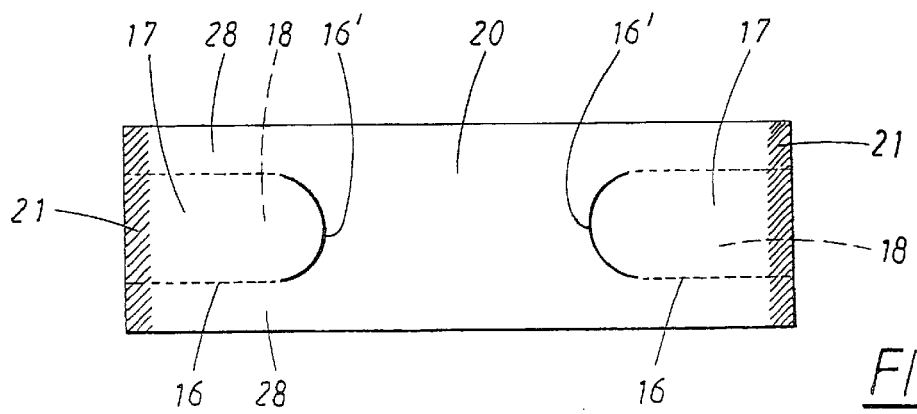
FIG. 6 shows a band of material having fastening tabs according to the invention.

FIG. 6 shows a material strip 20 of somewhat different configuration from the material strips described in connection with the nappies shown in FIGS. 1–5. The material strip 20 is provided with perforations 16, which demarcate two fold-out tabs 17 from the rest of the strip 20. The material strip 20 is intended to be fixed by its ends 21 to a nappy, for example by glue or welding. Moreover, the material strip 20 is fixed to a nappy within the sections which do not form the fold-out tabs 17. As shown in the figure, a section 16' of the perforation 16 can be cut or punched to make it easier to grip the fold-out tabs. Each tab 17 comprises fastening members 18, for example in the form of a VELCRO tape, or an adhesive surface. In FIG. 6, the fastening members 18 are arranged on the side of the material strip 20 which is facing away from the observer of the figure.

The tabs 17 in FIG. 6 differ from the tabs previously described by virtue of the fact that the width of the tabs 17 is less than the width of the material strip 20. This means that there are sections 28 of the material strip 20 which extend in the longitudinal direction of the tabs 17, on both sides of each tab 17. Such an embodiment can be advantageous for increasing the stability of the fastening member and for obtaining a somewhat stiffer waist section of the nappy. Should the material strip 20 be elastic, it also means that a certain elastic effect remains along the whole of the length of the material strip, even once the tabs are torn open and folded out.

The strip 20 can be fixed with the fastening members 18 facing inwards towards the nappy or outwards away from the nappy, depending on the positioning of the strip 20 in relation to the inside or outside of the nappy and the positioning of the receiving member or receiving members. It is obviously not necessary for the material strip to be continuous, but rather divided strips, as described in connection with FIGS. 1 and 4, can alternatively be used. Correspondingly, the receiving region can also obviously be configured as a continuous region or as separate receiving regions for each fastening tab 17.

Even though the fastening tabs according to the invention have been described in connection with VELCRO members, the principle of tabs which are formed by the detachment and folding-out of a part of a material piece can obviously be applied with other types of fastening members, for example adhesive fastening members, snap fasteners, buttons/buttonholes, clasp/eye, etc. Combinations of different types of fastening members are conceivable within the scope of the invention. The fastening members can be arranged over the whole or parts of the fold-out tabs. If the fastening members are hook or loop surfaces, or glued regions, these can be arranged as continuous surfaces, or as a pattern of two or more regions.

One method of producing a product of the kind shown in FIG. 5 and having fastening tabs 17 and a receiving surface formed from the same material is by fixing material strips 50, having an extent transversely to a production line of continuous products, at regularly spaced intervals to the production line in sections comprising the first end section 7 of a product and the second end section 8 of an adjacent product. The material strip 50 is applied to the liquid-tight surface layer 3, i.e. on the side of the product which shall be facing away from the body of the user during use. The part of the material strip 50 which is fixed to the first end section 7 of a product comprises two perforated lines 16 for the formation of two tabs 17 which can be folded out from the strip 50. Each fold-out tab 17 comprises first fastening members 18 on the side of the material strip 50 which, prior to folding-out, is facing away from the liquid-tight surface layer 3. The part of the material strip 50 which is fixed to the second end section 8 of a product comprises a second fastening member 19. After the material strips 50 have been fastened, the material web is cut between the first end section 7 of a product and the second end section 8 of an adjoining product, whereby individual products are obtained having a first fastening member 18 on the first end section and a second fastening member 19 on the second end section. If the material strip 50 is elastic, it also forms waist elastics on the product.

It is also conceivable for the second fastening member to be constituted by a plurality of separate fastening members. It can also be desirable for the second fastening member to be placed on the side of the absorbent product which is facing the user during use.

The invention shall not be deemed to be limited to the illustrative embodiments here described, but further variants and modifications are conceivable within the scope of the patent claims. For example, the invention is applicable to absorbent products other than the nappies described in the examples. Furthermore, all conceivable combinations of the described illustrative embodiments are intended to be covered by the invention.

The securement of the strip, which securement also constitutes a fold line for the tab, has to be strong enough to prevent the strip from coming loose when the tab is folded out, or when the absorbent product is used.

What is claimed is:

1. An absorbent product having a substantially elongated shape and further comprising:

a liquid-permeable surface layer;

a liquid-tight surface layer; and an absorption body arranged between the surface layers;

the product further having longitudinal side edges, transverse end edges, a first end section, a second end section, a crotch section lying between the end sections;

two non-folded material strips in the first end section and extending in the transverse direction of the product, each of said material strips being directly fixed permanently at its ends to the first end section;

a fastening tab constituting a part of each of the material strips and demarcated from the rest of the associated material strip by means of a tear line between the fixed ends and extending substantial transversely to the transverse direction of extent of the associated material strip, each fastening tab including a first fastening member; and a second fastening member on the second end section of the product and arranged so as to interact with each first fastening member in order to bind together the product into a briefs shape.

2. The absorbent product according to claim 1, in which each tear line comprises a perforation or other material weakening.

3. The absorbent product according to claim 1, in which each of the material strips is fixed to the liquid-tight surface layer.

4. The absorbent product according to claim 1, in which each of the material strips is fixed to the liquid-permeable surface layer.

5. The absorbent product according to claim 1, in which each of the material strips comprises elastic material.

6. The absorbent product according to claim 1, in which the fastening members each comprise a mechanical fixing member.

7. The absorbent product according to claim 1, in which each first fastening member comprises an adhesive and the second fastening member comprises a receiving surface for the adhesive.

8. The absorbent product according to claim 1, in which one of said first fastening members is arranged on each side edge of the product.

9. The absorbent product according to claim 1, further comprising elastic members arranged along a part of each transverse end edge and forming waist elastics; and in which the material strips are below the elastic members in the first end section.

* * * * *